Figure 1:
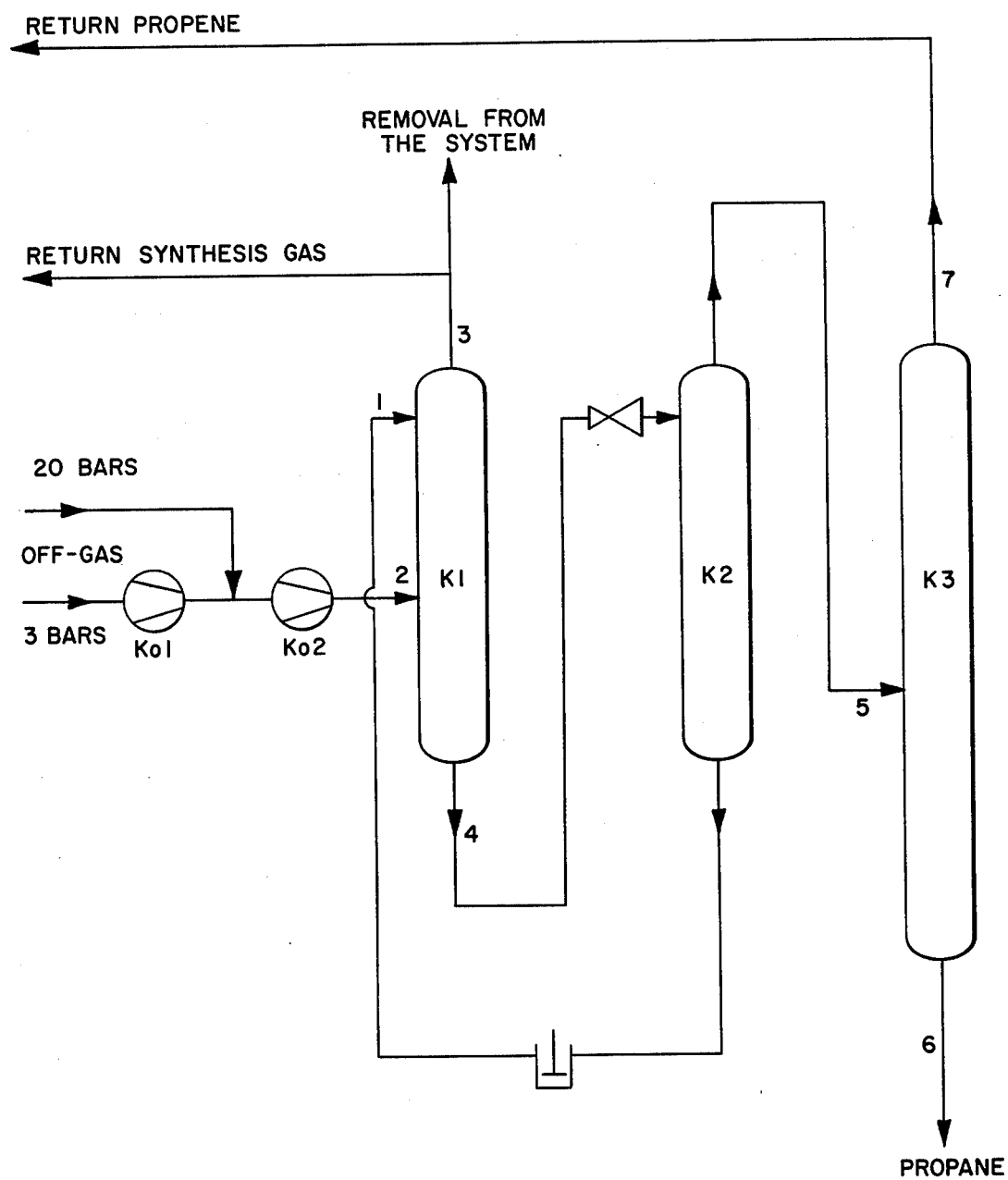

United States Patent [19]

Sridhar

[11] 4,210,426
[45] Jul. 1, 1980

[54] PROCESS FOR RECOVERING PROPENE AND PROPENE/PROPANE MIXTURES FROM THE OFF-GASES FROM THE HYDROFORMYLATION OF PROPENE

[75] Inventor: Srinivasan Sridhar, Marl, Fed. Rep. of Germany

[73] Assignee: Chemische Werke Huls Aktiengesellschaft, Fed. Rep. of Germany

[21] Appl. No.: 958,505

[22] Filed: Nov. 7, 1978

[30] Foreign Application Priority Data

Nov. 8, 1977 [DE] Fed. Rep. of Germany ....... 2749890

[51] Int. Cl.$^2$ .............................................. B01D 19/00
[52] U.S. Cl. ......................................... 55/68; 55/66; 568/909; 568/917; 568/451; 568/453
[58] Field of Search .............................. 55/68, 66, 89; 260/604 HF, 677 A; 568/909, 917

[56] References Cited

U.S. PATENT DOCUMENTS

| | | | |
|---|---|---|---|
| 3,338,974 | 8/1967 | Piacenti et al. | 260/604 HF |
| 3,369,050 | 2/1968 | Greene | 260/604 HF |
| 3,520,937 | 7/1970 | Moell et al. | 260/640 HF |
| 3,658,904 | 4/1972 | Kuper | 260/677 A |

*Primary Examiner*—Norman Yudkoff
*Attorney, Agent, or Firm*—Craig & Antonelli

[57] ABSTRACT

A process for recovering propene and propene/propane mixtures from the off-gases obtained from the hydroformylation of propene involves contacting the off-gases with a liquid absorbent comprising at least one of the liquid substances formed during the hydroformylation of propene to absorb the propene and propane and thereafter desorbing these gases from said liquid substances.

27 Claims, 2 Drawing Figures

PROCESS FOR RECOVERING PROPENE AND PROPENE/PROPANE MIXTURES FROM THE OFF-GASES FROM THE HYDROFORMYLATION OF PROPENE

When propene is subjected to hydroformylation, i.e. an Oxo reaction at 50° to over 200° C. and pressures as low as 18 bar and as high as over 200 bar, gas mixtures are obtained in addition to the liquid reaction products such as n-butyraldehyde, i-butyraldehyde, n-butanol and i-butanol. These gas mixtures consist of the unconverted components carbon monoxide, hydrogen and propene and also of propane, some of which is contained in the feed propene as an impurity and some of which is formed by hydrogenation of propene. These gas mixtures have hitherto been burned as off-gases, since the recovery of propene, CO and $H_2$ from the off-gases has hitherto not been considered necessary (Chemie-Ing.-Technik 41 (1969) No. 7, page 976). It is true that it has been attempted to use these gas mixtures together with the i-butyraldehyde obtained as by-product, in order to produce the synthesis gas, (i.e. carbonmonoxide and hydrogen), olefin, i.e. propene, and hydrogen required for the hydroformylation. However, after the enormous increase in the price of propene, the conversion of valuable propene to synthesis gas is no longer economical.

Taking into account the limited amounts of raw materials, and also with regard to environmental protection, recovery of propene and of propene/propane mixtures from the off-gases is, however, urgently required.

The recovery of propene and propane from the gas mixtures is possible by condensation or with the aid of a foreign substance as a recovery agent. However, temperatures far below −70° C. are necessary to effect complete condensation of propene and propane from these off-gases under low pressures and these temperatures can be obtained only by expensive refrigeration. Moreover, the moist off-gases would have to be thoroughly dried beforehand, in order to prevent icing-up at the low temperatures.

Separation processes which require a foreign substance as a recovery agent are, for example, extractive distillation with diethylpropionamide (DT-OS 1,948,433) and also absorption with methanol (DT-AS 1,147,247), with an aromatic compound (U.S. Pat. No. 2,572,341), with acetonitrile (GDR Pat. No. 91,480), with dimethoxytetraethylene glycol (U.S. patent application Ser. No. 633,843, Official Gazette 631, 283 (1950)) and with hydrocarbons (U.S. Pat. No. 2,894,601). However, all these processes would have the considerable disadvantage in that the gases recovered from the off-gases would require careful purification to remove the particular recovery agent, before the gases are re-employed in the hydroformylation. All these processes are therefore unsuitable for the recovery of propene and propene/propane mixtures from the off-gases from the hydroformylation of propene, since they are much too expensive and do not make possible an economical recovery.

The object of this invention is, therefore, to find a process which enables propene or propene/propane mixtures to be recovered in a simple and economical manner from the off-gases from the hydroformylation of propene.

This object is achieved according to the process of the invention, wherein propene and propane are recovered by absorption.

Surprisingly, it has been found that propene and propane can be absorbed in a simple and economical manner in the liquid hydroformylation products. Among the hydroformylation products, i-butyraldehyde and n-butyraldehyde are preferably suitable. As to the other hydroformylation products, it has been found that although the dissolving power of crude butanol is less, the low vapour pressure is, however, advantageous. Also mixtures of i-butyraldehyde, n-butyraldehyde and for crude butanol are suitable. In order to increase the absorption effect, higher pressures, for example 60 bars, and lower temperatures, for example 0° C., can be used. Since n-butyraldehyde is the valuable main product of the hydroformylation, i-butyraldehyde, which is more stable to heat, is used, in particular, as an absorbent belonging to the system obtained from the hydroformylation reaction. These absorbents belonging to the system have the great advantage that, after desorption, small amounts of these absorbents do not have to be separated off but can be recycled into the hydroformylation stage together with the propene recovered. Although i-butyraldehyde does not have the advantages of a selective absorbent, under pressures of 10 to 60 bars it is nevertheless a good solvent for separating the $C_3$ gases, i.e. propene and propane, from synthesis gas. In general, for example with 18% by volume of a $C_3$ constituent in the input gas, at normal temperature and with a number of theoretical separation stages of about 5, 2 to 15 kg of absorbent/$Nm^3$ of insoluble gases are employed.

Figure 2:
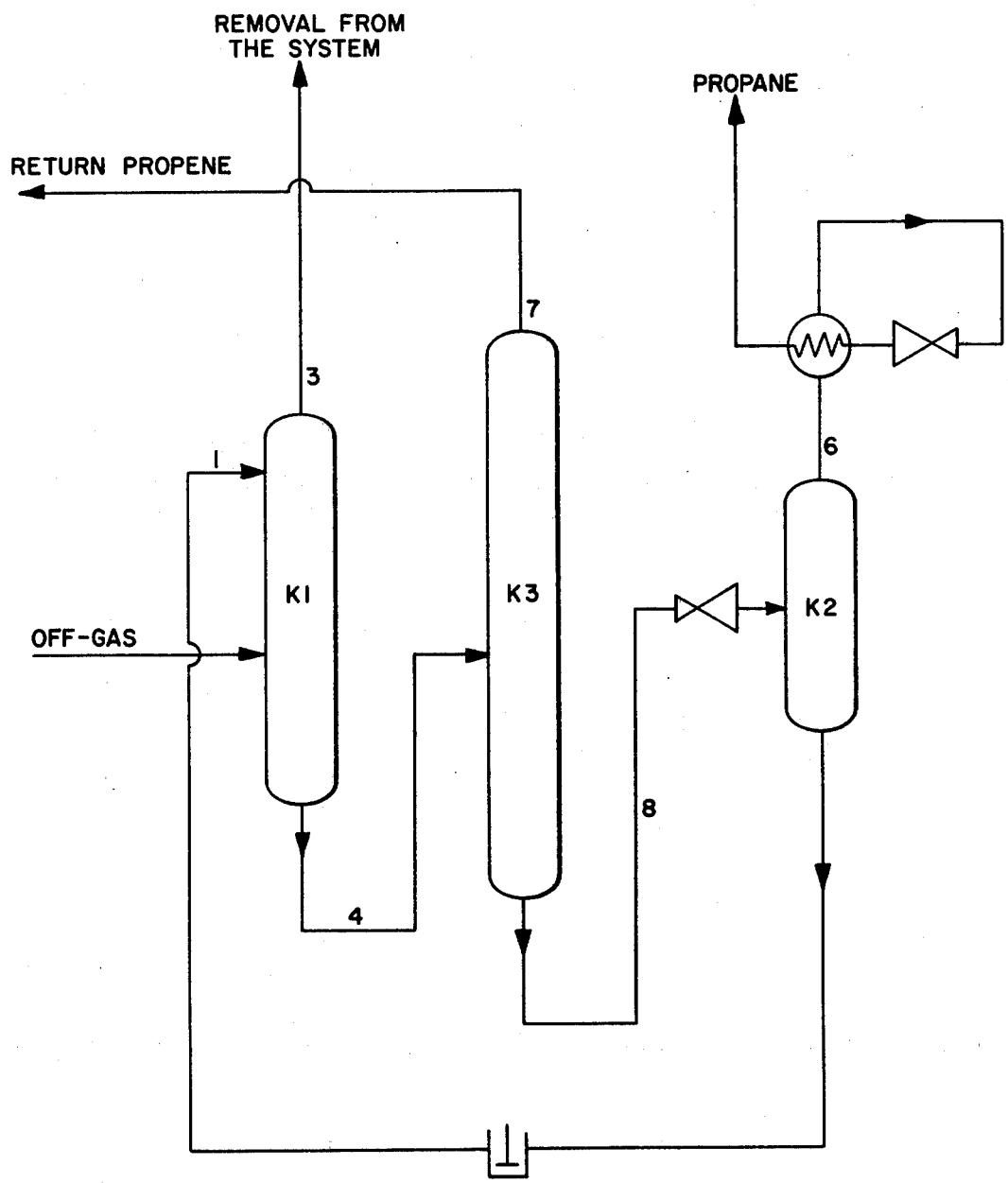

The invention will be further understood from the following detailed description and with reference to the drawings wherein:

FIG. 1 schematically shows one embodiment of an apparatus for effecting the recovery of $C_3$ gases, i.e. propene and/or propane from the off-gases resulting from hydroformylation of propene having three contact columns or treatment units; and FIG. 2 shows another embodiment of the apparatus for effecting the recovery of the $C_3$ gases.

The absorption is carried out under elevated pressure, preferably under 10 to 60 bars, and at temperatures of 0° to 50° C., preferably of 20° to 40° C. It is advantageous to carry out the absorption in an absorption column. In order to separate the $C_3$ gases from the synthesis gas, for example 7 kg of i-butyraldehyde/$Nm^3$ of off-gas containing 20% by volume of the $C_3$ constituent are employed in an absorption column with 5 theoretical separation stages under 35 bars (Distillation, Interscience Publ. Inc., New York (1951), page 6 ff; Design of equilibrium stage processes, Mc. Graw-Hill Chemical engn. series, Mc. Graw-Hill-Book Comp. New York (1963), page 79, 128, 142 and 143, example 5/2). With this procedure, a top product is obtained which is very largely free from the $C_3$ gases, which essentially consists of CO and $H_2$ and which can be recycled into the hydroformylation.

After the absorption, the absorbed gases, such as propene and propane, are together separated from the absorbent in a known manner, by lowering the pressure and/or raising the temperature, for example by raising the temperature up to just below the boiling point of the liquid. It is possible to separate off propene only by combining the desorption with a fractional distillation. The propane remains in the absorbent. The propene obtained after desorption is preferably recycled into the hydroformylation. Subsequently, the propane is separated off from the absorbent by distillation in a known manner. The free absorbent is recycled into the absorption stage.

With a propene and/or propane content in the off-gas, or in the input mixture for the recovery of, in each case, 3 to 10% by volume, the absorption is carried out under a total pressure of 25 to 60 bars, preferably of 30 to 40 bars, and at a temperature of 5° to 50° C., preferably of 20° to 40° C., the absorption taking place with a ratio of the product streams of i-butyraldehyde:insoluble gases, such as, for example, carbon monoxide, hydrogen and inert gases, of 2 to 5 kg/Nm³ and preferably of 3 to 4 kg/Nm³. Under these conditions, an absorption section or column with about 5 theoretical separation stages is required.

With a propene and/or propane content in the off-gas, or in the input mixture for the recovery of, in each case, 10 to 40% by volume, the absorption is carried out under a total pressure of 10 to 25 bars and preferably of 15 to 20 bars and at a temperature of 5° to 50° C. and preferably 20° to 40° C., the absorption taking place with a ratio of the product streams of i-butyraldehyde:insoluble gases of 5 to 10 kg/Nm³ and preferably of 7 to 9 kg/Nm³.

It is an essential advantage of the process that the propene and, additionally, the synthesis gas, are recovered in high yield in a simple manner, the recovered products optionally being recycled into the hydroformylation. The off-gases introduced into the recovery stage contain not only useful gases such as CO, $H_2$ and $C_3H_6$, but also ballast gases or inert gases such as $C_3H_8$, $N_2$, $CO_2$ and Ar. Therefore, when the non-absorbed gases (gas stream 3 in FIG. 1) are recycled into the hydroformylation, some of these must be removed from the system in order to avoid an enrichment of these gases in the cycle.

If this process is compared with the conventional low-temperature condensation process, it is found that with the condensation process it is possible to obtain an equally good yield of propene only when the gases pass through a final condensation stage at very low temperatures, for example of −90° C. under 35 bars, and this requires considerable expenditure on refrigeration. Moreover, with the refrigeration process, only fixed temperature stages are possible, while the absorption process of this invention provides scope for flexibility in the separating effect, by the choice of the column height and the rate of liquid flow.

In the case of hydroformylation under high pressure, the absorption can also take place under relatively high pressure. A high absorption pressure is economically advantageous in the case of off-gases with a relatively low $C_3$ content and also in the case of large amounts of gas. If the propene and propane are removed from the total off-gas, the residual gas can be recycled to the synthesis gas and some of it can also be removed from the system. The absorption can also be carried out under a comparatively low pressure and the portion of the gas to be removed from the system is fed to the absorption. A preferred separation of the propene from the stream of i-butyraldehyde, (propane already separated off in K3, see FIG. 2 and compare FIG. 1), enables low bottom temperatures to be used, and this is advantageous with regard to thermal efficiency.

EXAMPLE 1

(FIG. 1)

The hydroformylation off-gases, which are obtained from two different let-down stages at 20 bars and 3 bars, respectively, are combined and compressed in a compressor Ko 2 to 35 bars. The subsequent absorption of the $C_3$ gases in the absorption column or tower K1 takes place under this relatively high pressure. The input gas in line 2 containing about 12% by volume of propane constituents and about 6% by volume of propene constituents and 82% of relatively insoluble gases, i.e. hydrogen, argon, nitrogen, carbonmonoxide and carbon dioxide is scrubbed with isobutyraldehyde (from the hydroformylation after distillation) in counter-current, 3.64 kg of isobutyraldehyde being employed per Nm³ of the insoluble gases. After all the $C_3$ gases have been separated off in the absorption column K1, the synthesis gas, i.e. CO and $H_2$ is recycled directly into the hydroformylation reactor, (not shown).

The absorption in column K1 takes place at 35° C. and 35 bars. The isobutyraldehyde is introduced at the top of the column as stream 1. The gas mixture passes as stream 2 into the center of the column. The rectifying section of K1 serves for absorption. The isobutyraldehyde employed is $C_3$-free. After the absorption, only 1% of the propene introduced escapes together with the synthesis gas as stream 3. During the absorption, not only propene but also propane passes into the i-butyraldehyde stream 4. Independent conditions are thus produced: the substantially $C_3$- free synthesis gas is recycled into the hydroformylation. Approximately 2% of the amount of propane introduced remains in stream 3. Some of stream 3 (i.e. from 1 to 10%) is withdrawn from the system in order to remove inert gases ($N_2$, $CH_4$, Ar and the like) from the circulation.

The lower part of the absorption column K1 has a stripping action. The $C_2$ compounds and more readily volatile components are substantially separated off from the $C_3/C_4$ compound streams here. The prevailing pressure in the stripping section is 35 bars. the same as that in the absorption section. Since, however, hardly any volatile components are still present, the pressure is maintained only by the $C_3$ and $C_4$ components.

The separation of propene and propane from the isobutyraldehyde takes place in the desorption column or tower K2 by a $C_3/C_4$ distillation under 20 bars and at a top temperature of about 55° C. The isobutyraldehyde content ($C_4$ content) should be as low as possible in the top product in order to prevent unnecessary $C_4$ loss. If the aldehyde passes into the top product, it is removed from the system, with the stream of propane (stream 6), from the bottom of column K3 during the subsequent propene/propane separation. The bottom product of K2 must, on the other hand, be as far as possible completely $C_3$-free. Only then can the aldehyde be recycled as an effective absorbent to column K1 (stream 1).

In column K3, propene and propane are separated from one another by distillation at 45° C. and 20 bar press., as is known.

The propane leaves the system as stream 6 and can then be evaporated, let-down and burned, energy being generated. The propene, which is more than 96% pure (remainder propane), is recycled as stream 7 to the hydroformylation. 99% of the propene present in the off-gas is recovered.

If, in place of a ratio of 3.64 kg of i-butyraldehyde/Nm³ of insoluble gases (about 5 separation stages in column K1), only 2.22 kg/Nm³ were employed, the number of separation stages would be infinite. With only one separation stage, more than 150 kg of i-butyraldehyde/Nm³ would be necessary.

EXAMPLE 2

The input gas contains about 12% by volume of propane and about 6% by volume of propene. The remainder of the input gas has the same type of make-up as in Example 1. The process corresponds to the process described in Example 1. However, the absorbent employed is the crude hydroformylation product (discharge from the hydroformylation reactor), direct or as a part stream. The crude product has the following composition: 19.0% by weight of isobutyraldehyde, 60.1% by weight of n-butyrldehyde, 4.2% by weight of i-butanol, 7.9% by weight of n-butanol, 4.6% by weight of high-boiling compounds (monoester of i-butyric acid, octandiol and unknown compounds) and 4.2% by weight of water.

The absorption takes place under 35 bars and at 35° C. with 11 kg of the indicated crude product per Nm³ of insoluble gases and with about 5 separation stages; 99% of the propene is recovered. If less than 4 kg of the crude product/Nm³ were employed, an extremely high number of separation stages would be required (number of separation stages = ∞ at 3.55 kg/Nm³). With only 1 separation stage, 670 kg of the crude product would be necessary for a successful recovery.

EXAMPLE 3

The input gas contains about 12% by volume of propane and about 6% by volume of propene. The remainder of the input gas has the same type of make-up as in Example 1. The absorbent employed is n-butyraldehyde (hydroformylation product after distillation), using the process described in Example 1. The absorption is carried out at 35° C. under 20 bars, with about 5 separation stages and a ratio of 7.4 kg of n-butyraldehyde/Nm³ of insoluble gases; virtually complete absorption is obtained and 91% of the propene is recovered. With only 4 kg/Nm³ of n-butyraldehyde, the necessary number of separation stages would be infinite. With only 1 separation stage, 665 kg of i-butyraldehyde/Nm³ would be necessary.

EXAMPLE 4

The input gas contains about 12% by volume of propane and about 6% by volume of propene. The remainder of the input gas has the same type of make-up as in Example 1. The absorbent employed is crude butanol (hydroformylation product after distillation). The absorption is carried out under 60 bars at 10° C. with a ratio of 3.5 kg of crude butanol/Nm³ of insoluble gases, using about 5 separation stages. The other conditions correspond to those of Example 1. 99% of the propene is recovered. With 1.73 kg/Nm³, the separation stages of only 1, 160kg/Nm³ would be necessary.

EXAMPLE 5

(FIG. 2)

The input gas contains 15% by volume of propane and 15% by volume of propene. The remainder of the input gas has the same type of make-up as in Example 1. As in the other examples, this gas is washed in a column K1, which has 5 separation stages, with 8.35 kg of isobutyraldehyde (hydroformylation product after distillation)/Nm³ of insoluble gases in counter-current. The absorption of the $C_3$ gases takes place in the rectifying section under 20 bars and at 35° C. The $C_3$-free gas stream 3 passes to a combustion stage. The i-butyraldehyde stream 4 charged with $C_3$ gas is passed into the desorption column K3, where a propene/propane separation takes place at a top temperature of 50° C. and under 20 bars. The propene distillate is recycled as a liquid to the hydroformylation reactor. The propane is then separated from i-butyraldehyde in column K2 under a pressure of 6 bars and at a top temperature of 5° C. In this column, propane itself serves as the coolant for the condensation of the top product. The $C_3$-free i-butyraldehyde stream (stream 1) is pumped back into column K1 for absorption. 99% of the propene is recovered. With 3.9 kg of isobutyraldehyde/Nm³, the number of separation stages would be infinite. With only 1 separation stage, 148.5 kg of isobutyraldehyde 3 would be necessary.

What is claimed is:

1. A process for separating off and recovering propene and propene/propane mixtures from the off-gases from the hydroformylation of propene, said off-gases including carbon monoxide, hydrogen, propene and propane, which comprises passing said off-gases from the hydroformylation of propene to an absorbent, absorbing the propene and propane from said off-gases in the absorbent, which absorbent is comprised of at least one of the liquid substances which have formed during the hydroformylation of propene, and subsequently desorbing the propene and propane from said liquid substances.

2. A process according to claim 1, wherein the absorbent employed is i-butyraldehyde, n-butyraldehyde or the crude butanol obtained in the hydroformylation, or mixtures thereof.

3. A process according to claim 1, wherein the absorption is carried out using i-butyraldehyde, n-butyraldehyde or the crude butanol obtained in the hydroformylation, or in mixtures thereof as the absorbent, under elevated pressure, of from 10 to 60 bars, and at temperatures of 0° to 50° C.

4. A process according to claim 3, wherein the absorption is carried out at temperatures of 20°–40° C.

5. A process according to claim 1, wherein the absorbent employed is i-butyraldehyde.

6. A process according to claim 1, wherein the absorption is carried out using i-butyraldehyde as the absorbent under elevated pressure, of from 10 to 60 bars, and at temperatures of 5° to 50° C.

7. A process according to claim 5 or 6, wherein when the propene and/or propane content in the input mixture is 3 to 10% by volume in each case, the absorption is carried out under a total pressure of 25 to 60 bars and at a temperature of 5° to 50° C.

8. A process according to claim 7, wherein the absorption is carried out under a total pressure of 30 to 40 bars.

9. A process according to claim 8, wherein the absorption is carried out at a temperature of 20° to 40° C.

10. A process according to claim 7, wherein the absorption is carried out at a temperature of 20° to 40° C.

11. A process according to claim 7, wherein the absorption is carried out with a ratio of the streams of i-butyraldehyde:insoluble gases of 2 to 5 kg/Nm³.

12. A process according to claim 11, wherein said ratio is 3 to 4 kg/Nm³.

13. A process according to claim 5 or 6, wherein when the propene and/or propane content in the input mixture is 10 to 40% by volume in each case, the absorption is carried out under a total pressure of 10 to 25 bars and at a temperature of 5° to 50° C.

14. A process according to claim 13, wherein the absorption is carried out under a total pressure of 15 to 20 bars.

15. A process according to claim 14, wherein the absorption is carried out at a temperature of 20° to 40° C.

16. A process according to claim 13, wherein the absorption is carried out at a temperature of 20° to 40° C.

17. A process according to claim 5 or 6, wherein the absorption is carried out with a ratio of the streams of i-butyraldehyde:i soluble gases of 2 to 5 kg/Nm³.

18. A process according to claim 17, wherein said ratio is 3 to 4 kg/Nm³.

19. A process according to claim 5 or 6, wherein the absorption is carried out with a ratio of the streams of i-butyraldehyde: insoluble gases of 5 to 10 kg/Nm³.

20. A process according to claim 19, wherein said ratio is 7 to 9 kg/Nm³.

21. A process according to claim 1, wherein the propene and the propane are separately desorbed from the liquid substances.

22. A process according to claim 21, wherein the propene and the propane are separately desorbed from the liquid substances by first fractionally distilling the propene from the liquid substances and then distilling off the propane from the liquid substances.

23. A process according to claim 21, wherein after desorption of the propene the propene is cycled back into the reactor in which the hydroformylation of propene is being performed.

24. A process according to claim 1, wherein said off-gases also include nitrogen, carbon dioxide, methane and argon, and wherein off-gases not absorbed in said absorbent, including carbon monoxide and hydrogen, are cycled back into the reactor in which the hydroformylation of propene is being performed, to provide additional synthesis gas for the hydroformylation reaction of propene.

25. A process according to claim 24, wherein a portion of said off-gases not absorbed in said absorbent is withdrawn and not cycled back to said reactor, whereby enrichment of off-gases inert to said hydroformylation reaction of propene is avoided.

26. A process according to claim 25, wherein 1 to 10% of said off-gases not absorbed in said absorbent is withdrawn and not cycled back to said reactor.

27. A process according to claim 1, wherein the off-gases not absorbed in said absorbent is withdrawn and discharged.

* * * * *